US 9,357,947 B2

(12) United States Patent
deGreef et al.

(10) Patent No.: US 9,357,947 B2
(45) Date of Patent: Jun. 7, 2016

(54) FOOT FUNCTION SENSOR

(75) Inventors: Jules A. deGreef, Draper, UT (US);
David B. Beck, Draper, UT (US); John M. Forst, West Jordan, UT (US)

(73) Assignee: BEND TECH, LLC, Sandy, UT (US)

( * ) Notice: Subject to any disclaimer, the term of this patent is extended or adjusted under 35 U.S.C. 154(b) by 442 days.

(21) Appl. No.: 12/604,951

(22) Filed: Oct. 23, 2009

(65) Prior Publication Data

US 2011/0098605 A1    Apr. 28, 2011

(51) Int. Cl.
| A61B 5/103 | (2006.01) |
| A61B 5/117 | (2006.01) |
| A61B 5/11 | (2006.01) |
| A61B 5/00 | (2006.01) |

(52) U.S. Cl.
CPC ......... *A61B 5/1036* (2013.01); *A61B 5/1116* (2013.01); *A61B 5/6807* (2013.01); *A61B 5/6829* (2013.01); *A61B 2503/10* (2013.01); *A61B 2562/043* (2013.01); *A61B 2562/046* (2013.01); *A61B 2562/164* (2013.01); *A61B 2562/166* (2013.01)

(58) Field of Classification Search
CPC .. A61B 5/1036; A61B 5/1116; A61B 5/6807; A61B 5/6829; A61B 2526/166; A61B 2503/10; A61B 2562/164
USPC ............... 600/592, 301; 463/37; 607/48, 144
See application file for complete search history.

(56) References Cited

U.S. PATENT DOCUMENTS

| 5,157,372 | A | 10/1992 | Langford | 338/211 |
| 5,233,544 | A | 8/1993 | Kobayashi | 364/566 |
| 5,309,135 | A | 5/1994 | Langford | 338/211 |
| 5,408,873 | A * | 4/1995 | Schmidt et al. | 73/862.625 |
| 5,576,684 | A | 11/1996 | Langford | 338/50 |
| 5,583,476 | A | 12/1996 | Langford | 338/211 |
| 5,697,791 | A | 12/1997 | Nashner et al. | 434/247 |
| 5,789,827 | A | 8/1998 | Rawley et al. | 307/9.1 |
| 6,015,163 | A | 1/2000 | Langford et al. | 280/735 |
| 6,236,301 | B1 | 5/2001 | Langford et al. | 338/6 |
| 6,392,527 | B1 | 5/2002 | Gilano et al. | 338/2 |
| 6,481,432 | B2 | 11/2002 | Rushton et al. | 124/49 |

(Continued)

FOREIGN PATENT DOCUMENTS

WO    WO 2013/113122    8/2013    ......... A63B 69/36

OTHER PUBLICATIONS

International Search Report and Written Opinion issued in corresponding PCT Patent Appln. Serial No. PCT/US15/53285, dated Dec. 28, 2015 (12 pgs).

*Primary Examiner* — Max Hindenburg
*Assistant Examiner* — Jonathan M Foreman
(74) *Attorney, Agent, or Firm* — Hayes Soloway P.C.

(57) ABSTRACT

A system for measuring the force of the feet of a user upon the support surface of an item of footwear for each foot at multiple locations has a plurality of sensors each predictably varying in resistance upon application of a force thereto. The sensors send signals reflective of the force to an A-D converter. The digitalized signals reflective of the resistance and in some cases deflection are sent to a receiver for storage in a memory and for further transmission to a computing device to compute and display the force at each of the multiple points. An accelerometer may also be combined proximate to or attached to the insert to supply signals reflective of the acceleration and which can be used to calculate and display other information including acceleration, speed and distance.

21 Claims, 6 Drawing Sheets

(56) References Cited

U.S. PATENT DOCUMENTS

| | | | |
|---|---|---|---|
| 7,219,380 B2 | 5/2007 | Beck et al. | 5/713 |
| 7,292,151 B2 * | 11/2007 | Ferguson et al. | 340/573.1 |
| 2002/0173364 A1 | 11/2002 | Boscha | 473/131 |
| 2003/0120353 A1 * | 6/2003 | Christensen | 623/26 |
| 2006/0085047 A1 * | 4/2006 | Unsworth et al. | 607/48 |
| 2008/0287832 A1 | 11/2008 | Collins et al. | |
| 2013/0116808 A1 | 5/2013 | Molinari et al. | 700/91 |
| 2013/0196769 A1 | 8/2013 | Shocklee | 463/37 |

\* cited by examiner

FOOT FUNCTION SENSOR

BACKGROUND OF THE INVENTION

1. The Field of the Invention

This application relates to a system used to measure the functioning of a user's feet when involved in activity and more particularly includes a device for positioning between the support surface of footwear and the foot of a user supported on the footwear to sense the functioning of the foot as the user moves that foot. More particularly, this application relates to a sensor pad that is positioned on or above the support surface of an item of footwear that detects the force exerted by at least one portion of the user's foot with the user positioned on and supported in an upright position on the footwear and also to sense the velocity and acceleration of the user's foot.

2. State of the Art

When standing upright, a human is typically supported by or deemed to be standing on his or her two feet. It is generally accepted that each foot has three areas of support, namely the heel, the ball (behind the big toe) and the outside (behind the little toe). It is also known that many people have legs of different length and feet of different size. In turn, the weight of an upright person may not be evenly distributed between left and right legs and/or, in turn, between left and right feet. In addition, the feet of a user may be oriented so that the three areas of support are not in a plane. In turn, the weight of the user is borne unevenly between the three points of support.

A human or other biped can engage in a wide variety of activity that involves operation of the one or both of the user's feet. That is, a user can engage in walking, jogging and running. In sports, the user is typically involved in one of these activities in one form or in combinations. For example, sports that involve movement of the feet directly and indirectly include, but are in no way limited to, track and field, skiing, skating, bowling, soccer, football, basketball, hockey, lacrosse, golf, baseball, tennis, squash and fencing. In effect, all such activity involves movement of the body and/or feet in a way that the weight or force on the feet and, in turn, on the points of support will vary. For example, in tennis, the user may run quickly and stop abruptly to reach a ball.

For many reasons it is desirable to know the relative distribution of forces between each of the points of support of a foot, the distribution of weight between feet, and the weight on each foot. Devices to effectively measure the weight on each of the points of support and the distribution of weight between feet as well as to measure the forces or weight one each foot are unknown. At the same time, it may be desired to know the velocity of the foot and the acceleration of the foot as it is being moved by the user in one direction or another to evaluate the movement.

SUMMARY OF THE INVENTION

A sensing system includes an insert for placement between the support surface of an item of footwear and the foot of a user. The insert includes a pad sized for positioning on the support surface of the item of footwear. At least one sensor is associated with the pad and positioned to sense the deflection of the support surface effected by the user's foot. The sensor is also configured to transmit or supply detection signals each reflective of the deflection of the support surface.

Connector means are provided to connect to the sensor to receive the detection signals and to transmit the detection signals. A converter means is provided and connected to receive the detection signals from the connector means and configured to supply digital detection signals reflective of the detection signals received from the sensor. The system also has a memory means in communication with the converter means to receive the digital detection signals, to store the digital detection signal and to provide the digital detection signals to the computer.

The system also includes computer means configured to receive the digital detection signals and to compute the deflection of the support surface reflected by the digital detection signal. The computer has a display associated with it and is configured to display a perceivable image reflective of said deflection of said sensor. The image may show units of deflection, force, distance or some other data that can be calculated from the deflection signal. A power supply means is also provided to supply power to the sensor, the converter means, the memory means and the computer means.

In preferred arrangements, the sensor is positioned proximate a support point of the foot. In more preferred arrangements, a plurality of sensors and more preferably three sensors are positioned proximate different support points of the foot.

While the sensor can be an FSR (force sensitive resistor) or other piezo resistive device, it is most preferred if the sensor includes a substrate with a resistance material deposited thereon. The resistance material is of the type that predictably changes its electrical resistance upon deflection. The connector means are each connected to, and preferably to the opposite ends of the resistance material.

The memory means is configured to store the digital deflection signals in any one of several ways. It may use a removable memory card (e.g., an SD (Secure Digital), Compact Flash, Micro SD or similar), a flash drive or a CD. It may also have a hard memory with a suitable sized "hard" memory or random access memory chips (RAM).

In an alternate arrangement, the digital detection signals can be sent over a wire to the memory means. Alternately and preferably, the insert includes a first transmitter connected to receive the digital detection signals from the converter and to transmit first transmitted signals reflective of said digital detection signals. The memory means includes a first receiver configured to receive the first transmitted signals and to extract and supply digital detection signals for storage.

The memory means may also include a second transmitter connected to receive the digital detection signals from the memory means. The transmitter is configured to transmit second transmitted signals. In turn, the computer means includes a receiver configured to receive the second transmitted signals and to supply extract said digital deflection signals for processing in to suitable signals for display.

In a highly preferred arrangement, the system includes an accelerometer mounted on the insert. The accelerometer is configured to sense the acceleration of the insert as it is moved by the user. The accelerometer is connected to supply an acceleration signal to the converter means which, in turn, supplies a digital acceleration signal to the memory optionally and preferably through the transmitter. The memory means is configured to receive and store the acceleration signal and to supply it to the computer means. The computer means is configured to receive said acceleration signal and to generate a display reflective of the acceleration. The computer can by suitably integrating and using time date calculate velocity (speed), rate of movement, stride (length and time) and acceleration. That is, the acceleration signal can be processed to produce other information.

In preferred structures the insert may be a pad that is, in effect, an insole that can be inserted into a shoe of the user. Of course, it should be understood that the preferred configuration includes an insert or pad for the left foot and one for the right foot.

DESCRIPTION OF THE DRAWINGS

In the drawings, which illustrate what are presently regarded as the preferred embodiments of the invention.

DESCRIPTION OF THE ILLUSTRATED EMBODIMENTS

Figure 1:
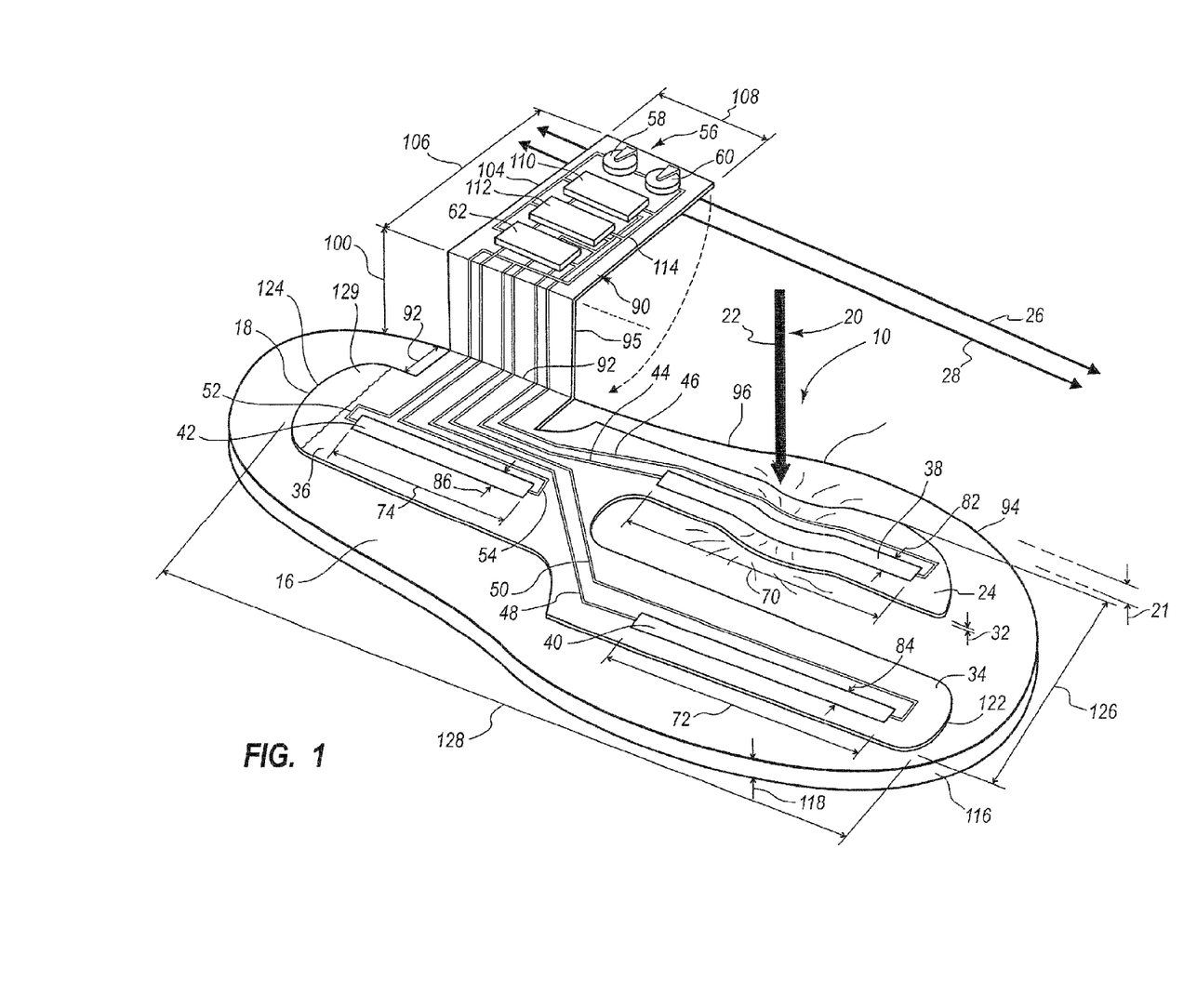
FIG. 1 is a perspective view of an insert of the present invention.

In the drawings, FIG. 1 depicts in perspective an insert 10 sized for placement on a support surface of an item of footwear. As used herein, footwear includes anything that may be worn by the user on one foot or both of his or her feet and has some form of support structure between the bottom 12 of the user's foot 14 (FIG. 2) and a support surface 16 (FIG. 1). Thus, footwear as contemplated herein includes virtually all structures, devices, items and/or things by whatever name that are placed on a foot or the feet of a user including shoes, boots, and sandals. In preferred applications, the support surfaces that support the user's foot are deflectable in some fashion as discussed more fully hereinafter.

Figure 2:
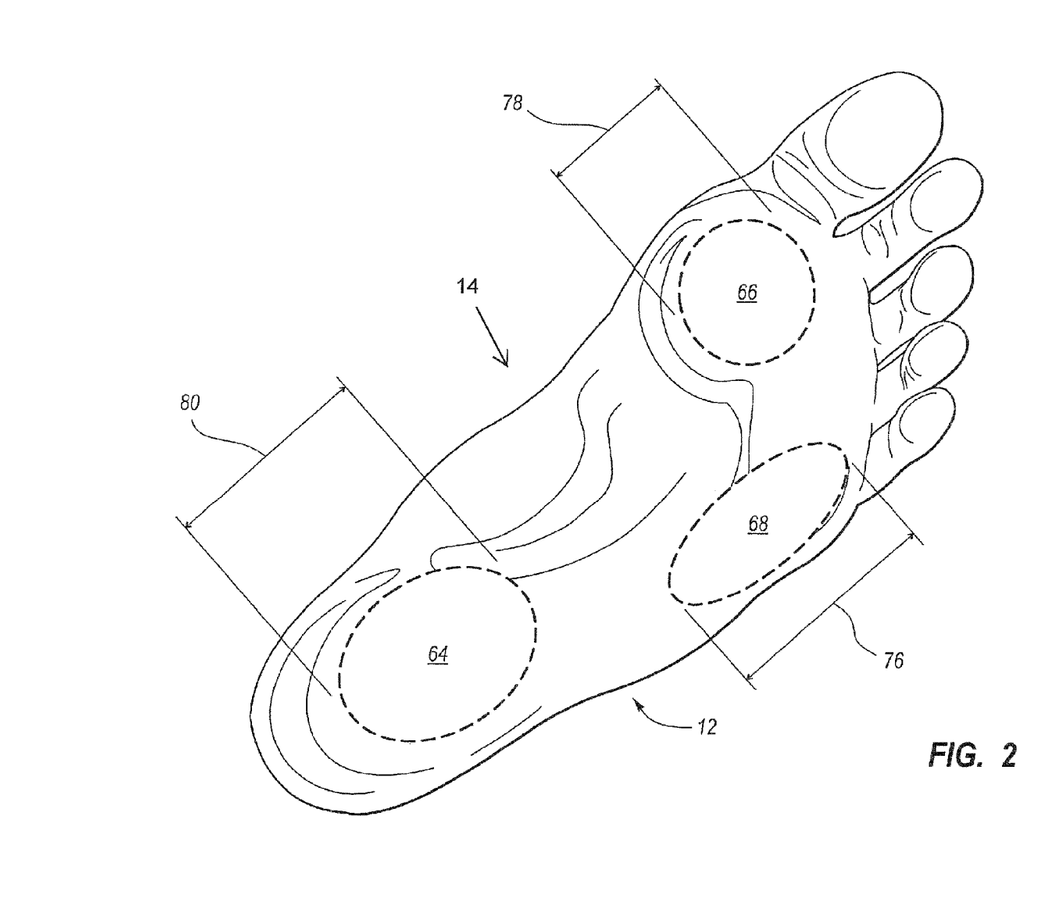
FIG. 2 is a perspective view of the bottom of a foot.

The user discussed in connection with the preferred embodiments is a typical human or hominid. The user may be male or female and of any age so long as the user is able to stand upright and walk. Further, it is within contemplation that the user may include quadrupeds and other hominoids such as apes. Further, it should be understood that the principles of the invention apply to both feet even though FIG. 2 shows the bottom 12 only of the foot 14 which is the left foot of a user. The right foot has not been illustrated for simplicity.

The insert 10 of FIG. 1 has a substrate or base 18 that is made of an electrically insulating material. At the same time, it is durable and long wearing while being flexible and elastically deformable. Various polymers such as polyimide, polycarbonate and polyesters are believed to be particularly suitable. For example, E.I. duPONT and de NEMOURS & Co. of Wilmington Del. (DuPont) offers Kapton® film (a polyimide) and Mylar® film (a polyester). Both are believed to be suitable for use.

The base 18 is flexible or elastically deformable much like a piece of paper. That is, the base 18 may be bent or twisted or deflected upon application of a suitable force. As shown in FIG. 1, the outer element 24 of the base 18 is moved downwardly 20 a distance which is the deflection 21 by force 22 to form detent 30. Thus, the outer element 24 moves from its normal position with a non deflected length 26 to a deflected length 28 as the detent 30 is formed by the force 22. The base 18 is not elastically deformable in that it may not be pulled to vary its dimensions like a rubber band.

The insert 10 of FIG. 1 has an outer element 24 and an inner element 34 both of which are connected to the heel element 36. While the base 18 is preferably unitarily formed, it may be formed in segments or parts. For example, one or both of the outer element 24 and the inner element 34 both may be separate and be joined to the heel element 36 by suitable means such as a piece of thin tape. Of course, different pieces of the base 18 also could be joined to together using suitable plastic welding procedures.

The base 18 of the insert 10 has a thickness 32 that is substantially uniform. However, the thickness 32 for the heel element 36 may be different from the thickness 32 of either the outer element or the inner element. The thickness 32 for the base 18 as shown is may be from about 0.1 inch to about 0.01 of an inch. A relatively small thickness 32 is preferred for most applications in which the footwear encloses or surrounds the foot 14 (FIG. 2) like a typical shoe or boot.

The insert 10 of FIG. 1 has an outer sensor 38, an inner sensor 40 and a heel sensor 42. While three sensors are contemplated for the present invention, it should be understood that one sensor may be sufficient. Of course, in other applications two, three and even more sensors may be suitable. That is, the user may determine to use a number or quantity of sensors.

The outer sensor 38 is positioned on the outer element 24. The inner sensor 40 is positioned on the inner element 34; and the heel sensor 42 is positioned on the heel element 36. Each of the outer sensor 38, the inner sensor 40, and heel sensor 42 are formed from a material that is electrically conductive but yet has an electrical resistance that changes predictably as it is deflected. The material is preferably a conductive ink with epoxy mixture deposited in a way so that the ink deflects when the base 18 is deflected as the force 22 is applied. As the ink bends or deflects its electrical conductivity or resistance changes. As the support surface 16 is deflected to form, for example the detent 30, the material changes its resistance in value. Kirchhoff's Law is as follows:

$$E = R \cdot I$$

Where
E equals voltage in volts
R equals resistance in ohms
I equals current in amperes Thus, one can supply a voltage across the outer sensor 38, the inner sensor 40 and the heel sensor 42A and measure the resulting current through them. Alternately, one can apply a constant current and measure the resulting change in voltage. Suitable sensors to function as the outer sensor 38, the inner sensor 40 and the heel sensor 42 can be obtained from Flexpoint Sensor Systems, 106 West 12200 South, Draper, Utah 84020.

By applying an electrical signal such as a voltage or a current to any one and all of the outer sensor 38, the inner sensor 40 and the heel sensor 42, a corresponding change in the current or voltage can be detected that reflects the total amount of the deflection 21 of the outer sensor 38 and comparable deflection of the ball or inner sensor 40 and the heel sensor 42. In turn, power is supplied via conductors 44, 46, 48, 50, 52 and 54 from a power supply 56 made up of two batteries 58 and 60 wired in series. The deflection signals reflective of deflection 21 of outer sensor 38 and similar deflection signals of the inner sensor 40 and the heel sensor 42 are changes in current supplied to a converter 62. More specifically, one conductor 44, 48 and 54 is connected to the converter 62 while the other conductors 46, 50 and 52 are connected to the power supply 56. The converter 62 receives an analog electrical signal from each of the outer sensor 38, the inner sensor 40 and the heel sensor 42. The analog electrical signals are deflection signals which are converted by the converter into digital deflection signals. The converter 62 depicted is an analog to digital converter that is a 10 bit device that operates between 10 and 1000 Hz. The operation of suitable AD converters is known and for example, is described in *ABCs of ADCs (Analog to Digit al Converter Basics)* by Nicolas Gray of Nov. 24, 2003.

In FIG. 2, the foot 14 is shown to have three areas of support, namely the heel area 64, the ball area (behind the big toe) 66 and the outside area (behind the little toe) 68. When upright, the user is applying a force to the support surface through each of the three areas of support on both feet. Thus, if one knew how much support or force was being applied through each area for each foot, it could suggest and, in some cases, establish if a user was properly distributing the user's weight between the user's two feet and, if not, which foot was supporting more than the other. If one knew how much support or force was being applied through the different areas of each foot, the resulting pattern could suggest and in some cases establish if the structure of the user's foot was such that the weight on that foot was being improperly distributed to one or two areas rather than traditional or typical weight distribution between the three areas. A suitably qualified person could then take steps to cause inserts for a user's shoe to redistribute the weight between feet and even areas of support in each foot.

The amount of support at each of the heel area 64, the ball area 66 and the outside area 68 may vary not only when standing statically but also when the user is moving. Information about the support or force experienced at each of the support points when moving can be useful to determine how the user is moving in relation to some standard for comparison. With the information, steps can be taken to help develop, for example, either a training program or some prosthesis (e.g., shoe insert) to help. For example, a person who is not experienced or knowledgeable about the sport of running may run in a way so that the heel of the person's running shoe strikes or impacts the running surface before the other portion of the foot. There are some who believe that it is better if the ball area 66 and possibly the outside area 68 impact the running surface before the heel area 64. Again, a training program or some prosthesis may be devised to assist the person to develop better running skills.

From FIG. 1, it can be seen that the outer sensor 38, the inner sensor 40 and the heel sensor 42 are each positioned to register with the outer area 68, the inner or ball area 66 and the heel area 64 respectively. The outer sensor 38, the inner sensor 40 and the heel sensor 42 are each shown to have a length 70, 72 and 74 respectively that is selected to extend through or substantially through the lengths 76, 78 and 80 of the outer area 68, the ball area 66 and the heel area 64 of the foot 14 (FIG. 2). The outer sensor 38, the inner sensor 40 and the heel sensor 42 may optionally be oriented to extend transverse to or normal to their present orientation. In other words, the present orientation of the sensors along the length 26 of the base 18 is preferred as the deflection 21 is more easily detectable. However, the outer sensor 38, the inner sensor 40 and the heel sensor 42 could extend in any desired orientation with each sensor in a different relative to each other.

It may also be noted that the outer sensor 38, the inner sensor 40 and the heel sensor 42 each are essentially straight. However, other shapes or forms may be used. Further, the width 82, 84 and 86 of the sensors can vary together and separately. For example, for a narrower or smaller foot, the width 82, 84 and 86 of the sensors may be less or smaller because the overall width of the user's foot 14 is much smaller.

In FIG. 1, the base 18 has a side member 90 that has a first portion 91 extends outwardly a distance 92 selected to position the crease 93 at the edge 94 of the support surface 16 either on the outer side 96 or the inner side 98 of the support surface 16. The side member 90 also has a portion 95 that extends upwardly a distance 100 comparable to the height of a shoe or to extend over the side of sandal strap. A second crease 102 allows the outer portion 104 to extend a suitable distance 106 sized in width 108 to contain the converter 62, the power supply 56, an accelerometer 110 and a transmitter 112. An ADXL 2 axis accelerometer offered by Analog Devices Inc. of Norwood, Mass. 02062 is one possible device that could be used. The accelerometer 110 supplies an analog output reflective of the acceleration of the foot 14 (FIG. 2) to the converter 62 which is then converted to a digital signal for further transmission by the transmitter 112. The batteries 58 and 60 are small dry cell batteries including but not limited to those sometimes loosely referred to as "watch batteries" selected to supply suitable voltage for the interconnected components shown in FIG. 1.

The support surface 16 in FIG. 1 is shown as the upper surface 16 of an insole 116 that is typically positioned inside of shoes. It has a thickness 118 that may be about ⅛ of an inch and is often made of a resilient rubber-like or neoprene-like material. It is often selected so that it allows moisture to pass there through ("breathes") while providing suitable cushion comfort for the user. An insole 116 is typically sized to fit into a shoe or similar item of footwear. The material used for the support surface 16 varies and includes leather inserts and very rigid materials like wood. Preferably, the insole is formed of a material that is pliant and thus, has a durometer from about 10 to 20 on the Shore A scale. However, the support surface is any surface that supports a foot in connection with an item of footwear. For support surfaces which are quite rigid like wood, the illustrated outer sensor 38, an inner sensor 40 and a heel sensor 42 are not suitable because the deflection 21 will be essentially zero. In such a situation, a force sensitive resistor (see Adafruit Industries at www.adafruit.com/index) or another piezoelectric sensing device is used as a sensor rather than the flexible or deflectable outer sensor 38, inner sensor 40 and heel sensor 42 described. A force sensitive resistor can be used as one or more or all of the sensors of an insert like insert 10 with any of the insoles in selected applications as desired by the user.

The outer element 24, the inner element 34 and the heel element 36 are sized and shaped to fit into a suitable item of footwear. For example, the outer element of insert 10 has a rounded front corner 120, the inner element 34 has a rounded front 122 and the heel element has a rounded back 124 all selected to fit into a variety of footwear products. The width 126 and length 128 vary with the size of the footwear. Thus, an insert 10 for use in a size 14 EE shoe will be sized differently from one for use in a size 5 AA shoe. Also, the insert is typically fabricated by screening on the outer sensor 38, inner sensor 40 and heel sensor 42 and similarly adding the conductors 44, 46, 48, 50, 52 and 54. Thereafter a suitable coating 129 over the entire area of the insert 10 to make the insert in effect hermetically sealed so that moisture from the user's foot cannot effect the electrical performance of the insert 10 and the outer sensor 38, the inner sensor 40 and the heel sensor 42. Various liquid epoxy coatings and any suitable laminating material may be used to function as the coating 129.

Figure 3:
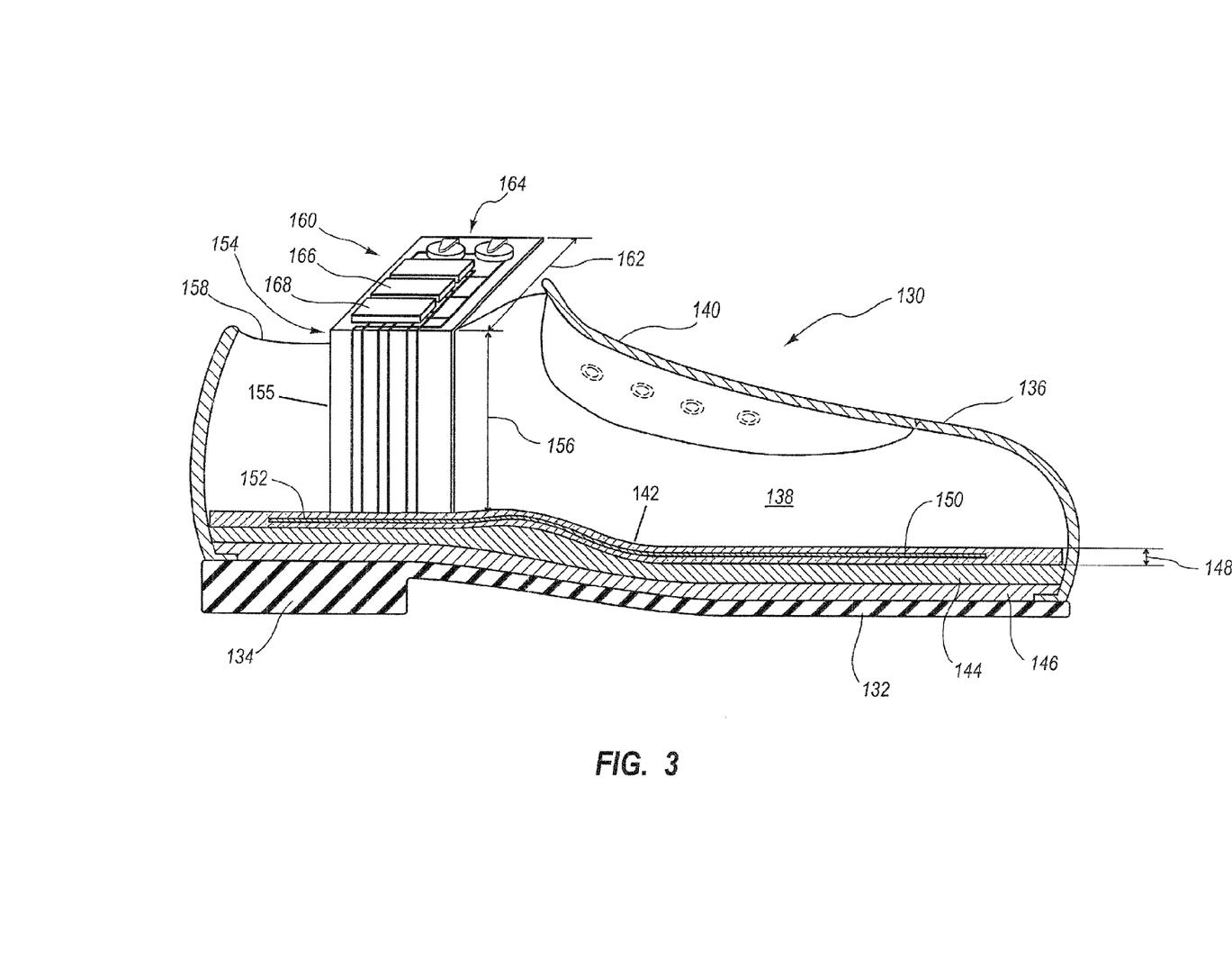
FIG. 3 is a cross section of an insert of the present invention in a shoe.

Turning now to FIG. 3, a man's shoe 130 is shown in cross section. It has a typical sole 132, heel 134 and body 136. The body 136 has a side wall 138 with a tongue 140. An insert 142 comparable to insert 10 (FIG. 1) is positioned above an insole 144 on top of a floor 146. The insert 142 is here shown to have a thickness 148 and to be formed out a resilient material. The outer sensor 150 and heel sensor 152 are shown potted in the material which is non breathing closed cell material and may be a type of epoxy material. The side member 154 has an upper portion 155 with a height 156 sized to reach the top 158 of the side wall 138. An outer portion 160 is unitarily formed with the upper portion 155 and sized in length 162 to extend less than the height 156 of the outer wall. The outer portion 160 has the power supply 164 coupled to a transmitter 166 and a converter 168. An accelerometer is not shown as it is optional.

Figure 4A:
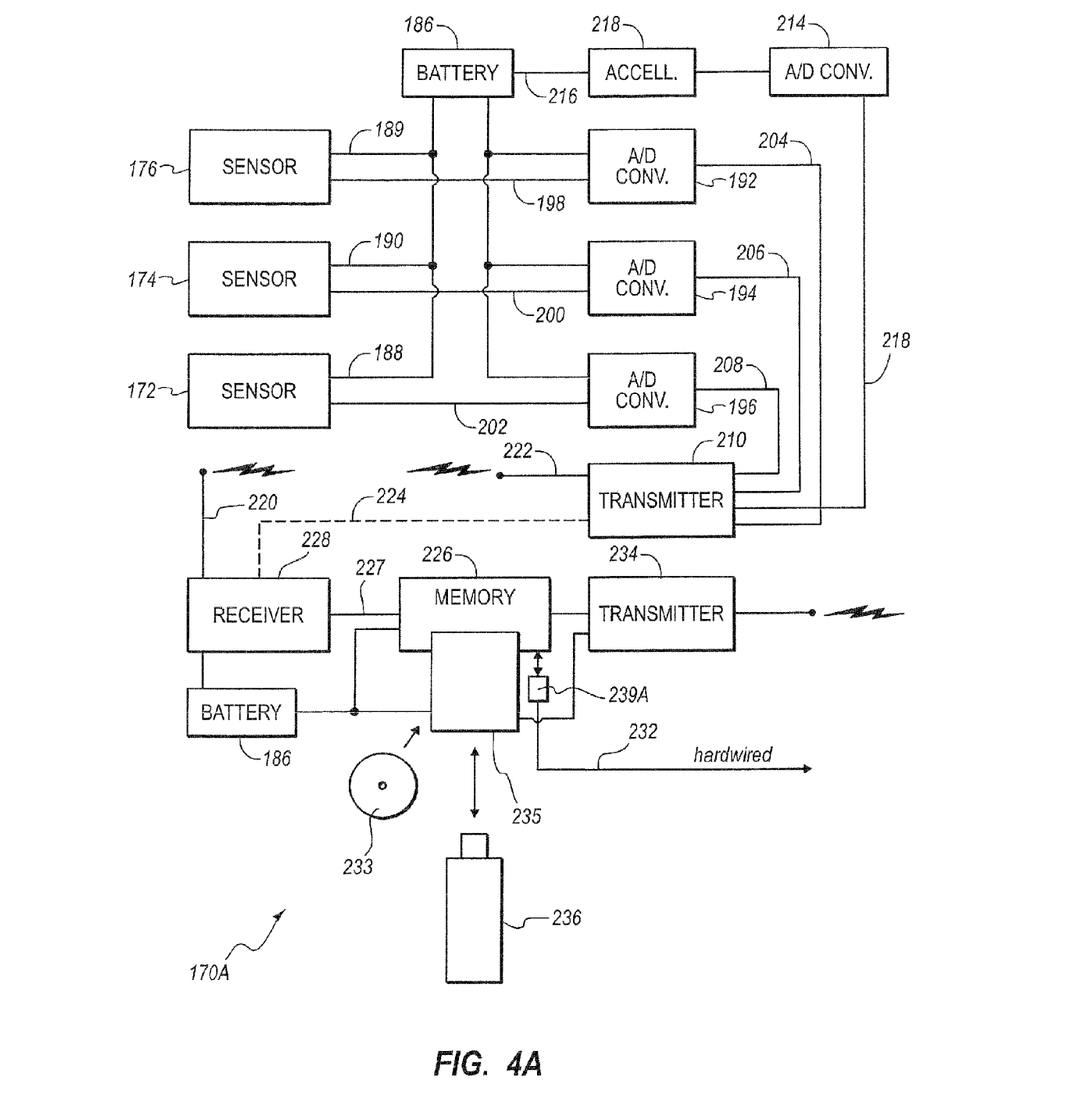
FIGS. 4A and 4B are a block diagram of a sensing system of the present invention.
Figure 4B:
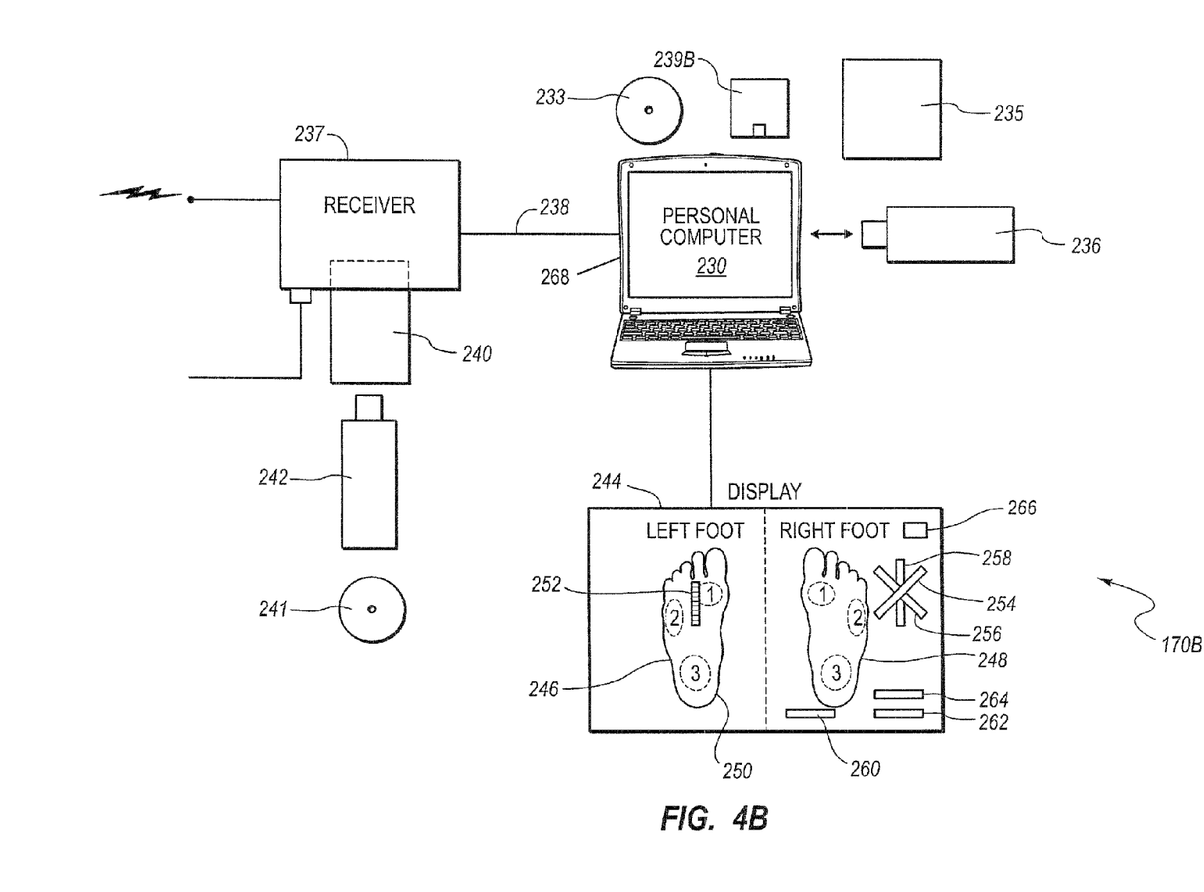
Figure 5:
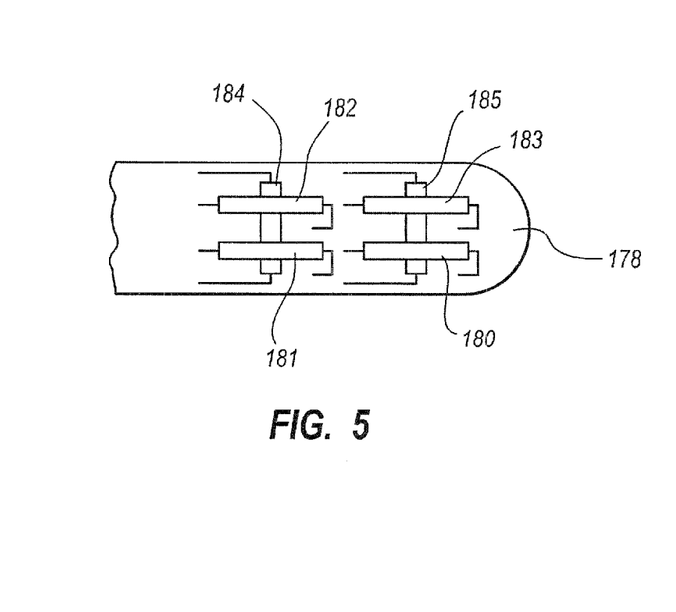
FIG. 5 is a perspective depiction of a belt mounted device for use as part of the present invention.

The block diagram of FIGS. 4A and 4B depicts a suitable sensing system 170A and 170B that has a plurality of sensors such as sensors 172, 174 and 176. Three sensors 172, 174 and 176 are depicted one for positioning at the ball area, the outside area and the heel area of the foot like foot 12 of FIG. 2. Of course, additional sensors can be used in other areas of the foot. For Example, FIG. 5 shows one part or element 178 of an insert like outer element 24 of base 18 having multiple sensors 180, 181, 182 and 183 oriented lengthwise (between the heel and toe of a foot) and sensors 184 and 185 oriented transverse thereto. Other configurations or patterns of sensors may be used as desired with the preferred sensors being of the type that predictably change resistance upon mechanical deflection such as the BEND SENSOR® detectors offered by Flexpoint Sensor Systems, Inc. of Draper, Utah.

The sensors 172, 174 and 176 are each connected to a power supply such as battery 186 via conductors 188, 189 and 190 as depicted in FIG. 4A. The sensors 172, 174 and 176 also are connected to analog to digital converters (A/D converters) 192, 194 and 196 via conductors 198, 200 and 202. The battery 186 supplies a voltage that is applied across the sensors 172, 174 and 176 which are electrical resistors that vary in resistance as they are deflected. In turn, the electrical current in the conductors 198, 200 and 202 going to converters 192, 194 and 196 varies with the deflection. The current is in effect an analog signal that the A/D converters 192, 194 and 196 convert to digital signals that are supplied via conductors 204, 206 and 208 to a transmitter 210 that processes the digital signals and transmits them as a radio frequency (RF) signal. The transmitter 210 may have a carrier and pulse or frequency modulate or it may process in any other suitable way. The digital converters preferred have a sample frequency of about 10 Hertz and an output that is supplied at a frequency that may vary from about 10 to 1000 samples or transmissions per second. In some cases, an RFID chip can be adapted as the transmitter.

FIG. 4A also shows an accelerometer 218 that is positioned on or about the foot. It could be located on the footwear, on a sock or on the lower leg. The accelerometer is a typical 3 axis device other single or two axis options may be applicable. A three axis device is used to measure the forward movement in three dimensional space of the wearer. Thus, it could be used to measure performance moving sideway or diagonally. A single axis device could measure movement in a forward/reverse direction only. The accelerometer supplies analog signals reflective of acceleration to an A/D converter 214 via conductor 216. The A/D converter supplies digital signals reflective of acceleration in the X, Y and Z axis via conductor 218 to the transmitter 210 for processing and transmission as an RF signal.

The RF signal with the digital signals from the AD converters is transmitted as a low energy signal to a receiving antenna 220 that is positioned within a few feet of the transmitting antenna 222. Alternately, the RF signal may be transmitted via a suitable RF cable 224 that is sized to extend between them with sufficient length to allow full movement of the involved limb. Alternately, the digital signals can be sent by conductors, 206, 208 and 218 directly to the memory 226 for storage and further processing as described hereinafter. Inasmuch as a wire extending from the foot area to another part of the body of the user is not desired or preferred, the RF signal is transmitted from antenna 222 to antenna 220.

Figure 6:
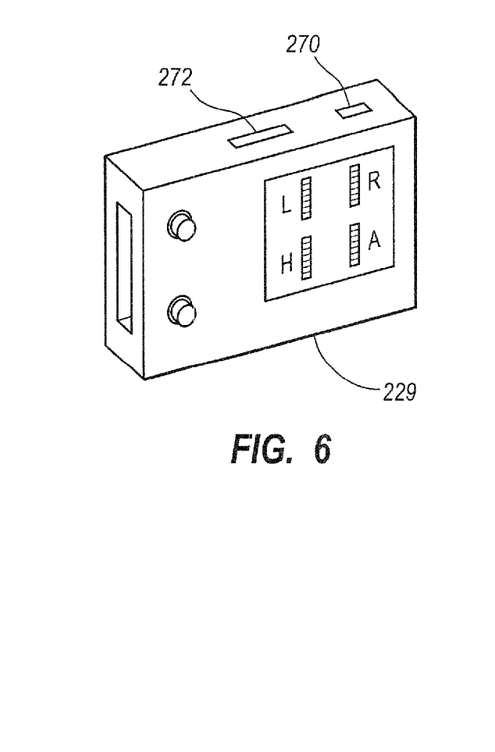
FIG. 6 is a depiction of a chassis as part of the present invention

The receiver 228 is positioned in a chassis like the chassis 229 seen in FIG. 6. It receives the RF signals and processes them to extract the digital signals reflective of deflection of each of the sensors 172, 174 and 176 as well as digital signals reflective of the acceleration in up to three axes, the X axis, the Y axis and the Z axis. The digital signals are supplied to the memory 226 via conductors 227 for storage until they are delivered to a computer (PC) 230 for further processing. The digital signals may be delivered to the PC 230 by any one of several means. They may be delivered by a wire 232 which is preferred if the PC is scaled back in size and packed directly into the chassis 229. Alternately, a transmitter 234 may be configured to process and transmit all the digital signals to a suitable receiver 237 (FIG. 4 B) connected to receive the digital signals and to extract them and transmit them to the PC via conductor 238.

The memory 226 may also include a suitable drive or drives to transfer the digital signals onto a CD 233, a memory chip 235 (e.g., made by SCAN DISC), and/or a flash drive 236. Of course, the CD, 234, the memory chip 235 and the flash drive 236 may be transported to the PC 230 to deliver the digital signals thereto. Alternately, the digital signals may be delivered by a wire like wire 232 that is removably connected to suitable port 239A and 239B associated with the PC. It should be noted that the receiver 237 could also be configured to transfer the digital signals onto a suitable medium such as a memory chip 240, a CD 241 or a flash drive 242. They may be transported to a suitably configured PC for further processing.

The PC 230 is programmed or configured to process the digital signals and produce signals to present a visually perceivable display 244. As seen in FIG. 4B, the display may be an image of a left foot 246 and a right foot 248 that has the areas depicted like areas 1, 2 and 3 where sensors have been placed by use of an insert like insert 10. The display 244 may be configured to produce an image reflective of deflection if each sensor like outer sensor 38, inner sensor 40 and heel sensor 42 (FIG. 1) by selecting different colors to display for selected ranges of deflection (e.g., red equals large, yellow equals medium, black equals little) or by changing or darkening rings 250 reflective of ranges of deflection or by a scale 252 that shows deflection on a scale. The display 244 may also display acceleration in the X axis 256, the Y axis 254 and the Z axis 258 for each foot. It may also produce an image 260 depicting velocity of the user and of each foot 262 and 264 as well as an image 266 displaying the total distance traveled from the time a person starts.

The PC 230 may be scaled or sized to include the memory 226 and to fit in the chassis 229. In that event, a suitable small screen 268 is provided that can include a series of bar graphs displaying values detected by the sensors. Images can alternate between left and right foot displays every few seconds. The chassis 229 may include batteries to power all with in components and be sized to be attached to the user at the waist by a suitable belt or clip. The chassis 229 may also be configured with suitable ports 270 and 272 to receive a CD or a flash drive to record digital signals for further use at a later time.

In use, a user may record all the digital signals connected to his during a particular period or event either in the PC 230 or in the memory 226 in the chassis 229. The digital signals may be compared to or with the data from and earlier or later period or event to show change or progress. This, in turn, may be used to suggest how the user may better move his or her feet to enhance his or her performance in connection with some activity. The user may learn to place more weight on the ball or the heel or to shift weight from the ball of the foot to the outside of the foot. Over time, information can be obtained and retained to show progress and help the user select exercises to improve or modify. In addition to sports and other related activity, the sensing system can be used in connection with physical therapy to monitor changes in strength and in range of motion following, for example, knee surgery and/or hip surgery and or tendon/ligament repair. In sports, it can be used to measure other foot performance values to determine corrective exercises and to compare one athlete to another or to a norm.

Those skilled in the art will recognize that many changes or variations may be made to the above illustrated system and the components thereof without departing from the spirit of the invention. Therefore, the details of the embodiment or alternatives illustrated and/or described are not intended to limit the scope of the appended claims.

The invention claimed is:

1. A sensing system for use with footwear, said sensing system comprising:
   an insert for placement on the support surface of the footwear for supporting the foot of a user of said footwear, said insert including:
      a base sized for positioning on the support surface of the footwear and configured to move and deflect to form a plurality of detents in said base and said support surface by a force applied by said user's foot at each of a plurality of support areas of said user's foot,
         said base being made of material that is deflectable upon application of each of said plurality of forces thereto at each of said plurality of support areas;
      a plurality of sensors associated with said base and positioned to sense deflection of said base with said support surface into each of said plurality of detents by said force applied at each of said plurality of support areas of said user's foot, each of said plurality of sensors being positioned and configured to transmit detection signals reflective of said deflection at its respective support area, each of said plurality of sensors including a substrate made of an electrically insulating material with a resistance material deposited thereon which resistance material is a layer of epoxy and conductive ink mixture that has opposite spaced apart ends and which resistance material predictably changes electrical resistance after application to said substrate upon said deflection;
      connector means connected to said to said resistance material of each of said plurality of sensors to receive said detection signals therefrom and to transmit said detection signals reflective of the deflection detected by each of said plurality of sensors;
      converter means connected to said connector means to receive said detection signals therefrom said converter means being configured to process said detection signals and to supply digital detection signals reflective of said deflection of each of said plurality of sensors;
      memory means in communication with said converter means to receive said digital detection signals therefrom, said memory means being configured to receive and store said digital detection signals and said memory means being configured to supply said digital detection signals;
      computer means connected to receive said digital detection signals, said computer means being configured to compute said deflection of said base at each of said plurality of support areas of said user's foot as reflected by said digital detection signals, and said computer means being configured to display a perceivable image reflective of said deflection of each of said plurality of sensors in each of support areas of said user's foot; and
      power supply means for supplying power to said insert, said converter means, said memory means and said computer means.

2. The sensing system of claim 1 wherein each of said plurality of sensors have a length that extends across its respective support area of said user's foot and wherein each of said plurality of sensors have a width that is less than said length.

3. The sensing system of claim 2 wherein said plurality of support areas includes three support areas and wherein said base includes three sensors each associated with one of said support areas positioned to sense deflection of said base into said detent at each of said three support areas of said user's foot.

4. The sensing system of claim 3 wherein said memory means is configured to receive one of a removable chip, a removable disc and a removable flash drive and is configured to store a plurality of said digital detection signals thereon.

5. The sensing system of claim 3 wherein said insert includes
   a first transmitter connected to receive said digital detection signals from said converter means and to transmit first transmitted signals reflective of said digital detection signals,
   wherein said system further includes a first receiver configured to receive said first transmitted signals and to supply said digital detection signals to said memory means, and
   wherein said power supply includes a first battery positioned to supply power to said insert and said converter means and a second battery positioned to supply power to said receiver and said memory means.

6. The sensing system of claim 5 wherein said system includes a second transmitter connected to receive said digital detection signals and configured to transmit second transmitted signals, and wherein said system includes a receiver configured to receive said second transmitted signals and to supply and extract said digital detection signals and supply them to said computer means.

7. The sensing system of claim 1 wherein said computer is configured to present a graphic image reflective of the value of said force detected by one of said plurality of sensors.

8. The sensing system of claim 1 wherein each of said support areas have a measurable planar dimension and wherein each of said plurality of sensors has a length that exceeds said measurable dimension.

9. The sensing system of claim 8 wherein each of said plurality of sensors has a width less than said measurable planar dimension.

10. The sensing system of claim 9 wherein each of said measurable dimensions is a diameter.

11. The sensing system of claim 1 further including an accelerometer attached to said insert, said accelerometer being configured to sense the acceleration of the insert as said insert is moved by the user and to supply acceleration signals to said converter means, wherein said memory means is configured to receive said acceleration signals, to store said acceleration signals and to supply said acceleration signals, and wherein said computer means is configured to receive said acceleration signals and to generate a display reflective of the acceleration detected by said accelerometer.

12. The sensing system of claim 1 wherein said substrate comprises a surface of said base.

13. The sensing system of claim 1 wherein said perceivable image includes means to visually display the relative value of the force at a selected support area.

14. An insert for use with footwear, said insert comprising:
a base sized for positioning on a support surface of the footwear, said base being made of material that bends in a foot support area upon application of a force thereto;
at least one sensor associated with said base and positioned to sense a deflection of said support surface by a force sufficient to cause said support surface to bend by said user's foot in said foot support area, said at least one sensor being positioned and configured to bend and to transmit a detection signal reflective of said bending in said foot support area, said at least one sensor including a substrate which extends across said foot support area and having a resistance material made of a conductive ink and epoxy mixture deposited thereon which resistance material predictably changes electrical resistance of said resistance material upon bending;
connector means connected to said resistance material of said at least one sensor to receive said detection signal from said at least one sensor and to transmit said detection signal;
converter means connected to said connector means to receive said detection signal therefrom, said converter means being configured to receive said detection signal and to supply a digital detection signal reflective of said bending; and
power supply means for supplying power to said sensor and said converter means.

15. The insert of claim 14 wherein said base includes a plurality of sensors each adapted to be positioned proximate a different support area of said user's foot.

16. The insert of claim 14 wherein said base includes three sensors each adapted to be positioned proximate each of three support areas of said user's foot.

17. The insert of claim 14 further including a first transmitter connected to receive said digital detection signals from said converter and to transmit first transmitted signals reflective of said digital detection signals and wherein said power supply includes a first battery positioned to supply power to said insert and said converter means.

18. The insert of claim 17 wherein said footwear is a shoe and wherein said base is an insole configured for positioning inside of said shoe.

19. A sensing system for use with left and right footwear, said sensing system comprising:
a pair of inserts, a left insert configured for placement between the left support surface of said left footwear and said user's left foot, and a right insert configured for placement between a support surface of the right footwear and said user's right foot, each of said left and right inserts including:
a base sized for positioning adjacent a respective support surface of said footwear,
at least one sensor associated with each of said pads, each of said at least one sensor being positioned to sense bending of a respective support surface in a support area caused by a force applied by said user's foot, one of said at least one sensors being configured to transmit left detection signals reflective of said bending associated with said left foot and the other of said at least one sensors being configured to transmit right detection signals reflective of said bending associated with said right foot, said at least one sensor further comprising a substrate made of an electrically insulating material and which extends across its support area with a resistance material made of a conductive ink and epoxy mixture and deposited thereon which resistance material predictably changes electrical resistance of said resistance material upon deflection,
connector means connected to said resistance material of said at least one sensor to receive said left detection signals and said right detection signals and to transmit said left and right detection signals, and
converter means connected to said connector means to receive said left and right detection signals therefrom, said converter means being configured to receive said left and right detection signals and to supply left digital detection signals and right digital detection signals;
memory means in communication with said converter means to receive said left digital detection signals and said right digital deflection signals therefrom, said memory means being configured to receive and store said left and right digital detection signals and to provide said left and right digital detection signals;
computer means configured to receive said left digital detection signals and said right digital detection signals and to compute the bending of said left support surface reflected by said left digital detection signals and said right support surface reflected by said right digital detection signals and configured to display perceivable images reflective of said bending of said sensors; and
power supply means for supplying power to said insert, said converter means, said memory means and said computer means.

20. A sensing system for use with footwear having a support that has support surface, said support being made of material that is deflectable by a force from each of a ball, an outside area and a heel of a user's foot, said sensing system comprising:
a ball sensor positioned to sense a deflection of said support surface proximate said ball of said user's foot;
an outside sensor positioned proximate said outside area of said user's foot; and
a heel sensor positioned proximate said heel as a user's foot;
each of said ball sensor, said outside sensor and said heel sensor being positioned and configured to extend across said ball, said outside area and said heel to bend upon deflection and to generate ball deflection signals, outside deflection signals and heel deflection signals respectively, each of said ball sensor, said outside sensor and said heel sensor further including a substrate made of an electrically insulating material with a layer of electrical resistance material made of a conductive ink and epoxy mixture and deposited thereon which electrical resistance material predictably changes electric resistance upon bending into an indentation caused by said user's foot;
connector means in communication with said electrical resistance material of each of said ball sensor, said outside sensor and said heel sensor to receive said ball deflection signals, said outside deflection signals and said heel deflection signals and to transmit said ball detection signals, said outside detection signals and said heel detection signals;

converter means in communication with said connector means to receive said ball detection signals, said outside detection signals and said heel detection signals therefrom, said converter means being further configured to supply digital detection signals reflective of said ball detection signals, said outside detection signals and said heel detection signals;

memory means in communication with said converter means to receive said digital detection signals therefrom, said memory means being further configured to store and provide said converted digital detection signals;

computer means in communication with said memory means and configured to receive said converted digital detection signals from said memory means and to form images that reflect the force applied by each of said ball, said outside and said heel of said user's foot; and power supply means for supplying power to said insert, said converted means, said memory means and said computer means.

21. A sensing system for use with footwear having a support that has a support surface, said support being made of material that is deflectable by a force from each of a ball, and a heel of a user's foot, said sensing system comprising:

a ball sensor positioned to sense a deflection of said support surface proximate said ball of said user's foot;

a heel sensor positioned proximate said heel of a user's foot;

each of said ball sensor and said heel sensor being positioned and configured to bend upon deflection and to generate ball deflection signals and heel deflection signals, respectively, each of said ball sensor and said heel sensor further including a substrate made of an electrically insulating material with a layer of electrical resistance material made of a conductive ink and epoxy mixture deposited thereon which electrical resistance material predictably changes electrical resistance upon bending into an indentation caused by said ball and said heel of said user's foot;

connector means in communication with said electrical resistance material of each of said ball sensor and said heel sensor to receive said ball deflection signals and said heel deflection signals and to transmit said ball detection signals and said heel detection signals;

converter means in communication with said connector means to receive said ball detection signals and said heel detection signals therefrom, said converter means being further configured to supply converted digital detection signals reflective of said ball detection signals and said heel detection signals;

memory means in communication with said converter means to receive said converted digital detection signals therefrom, said memory means being further configured to store and provide said converted digital detection signals;

computer means in communication with said memory means and configured to receive said converted digital detection signals from said memory means and to form sensible data that reflects the force applied by each of said ball and said heel of said user's foot; and power supply means for supplying power to said insert, said converter means, said memory means and said computer means.

* * * * *